US00PP36397P3

(12) United States Plant Patent
Hansen

(10) Patent No.: US PP36,397 P3
(45) Date of Patent: Jan. 14, 2025

(54) ***BERGENIA* PLANT NAMED 'FAIRYTALE ROMANCE'**

(50) Latin Name: *Bergenia*
Varietal Denomination: Fairytale Romance

(71) Applicant: Hans A Hansen, Zeeland, MI (US)

(72) Inventor: Hans A Hansen, Zeeland, MI (US)

(73) Assignee: Walters Gardens Inc, Zealand, MI (US)

( * ) Notice: Subject to any disclaimer, the term of this patent is extended or adjusted under 35 U.S.C. 154(b) by 476 days.

(21) Appl. No.: 17/803,929

(22) Filed: Jan. 26, 2023

(65) Prior Publication Data

US 2024/0260494 P1 Aug. 1, 2024

(51) Int. Cl.
*A01H 5/02* (2018.01)
*A01H 6/80* (2018.01)

(52) U.S. Cl.
USPC ..... Plt./409

(58) Field of Classification Search
USPC ..... Plt./263.1, 409
See application file for complete search history.

*Primary Examiner* — Karen M Redden

(57) ABSTRACT

A new and distinct Heartleaf *Bergenia* plant, *Bergenia* plant named 'Fairytale Romance' with a dense mounded habit, medium-sized, densely-arranged, deep-green, glossy, obovate, evergreen foliage, and large, apple-blossom-pink, campanulate flowers on large heavily-branched panicles over a long period beginning in spring. The flowers hold up well in the garden as a landscape plant or as cut flowers. The new plant has a medium growth rate and is naturally resistant to deer and rabbit foraging.

1 Drawing Sheet

Botanical designation: *Bergenia*.
Cultivar denomination: 'Fairytale Romance'.

STATEMENT REGARDING PRIOR DISCLOSURES UNDER 37 CFR 1.77(B)(6)

The first non-enabling disclosure of the claimed plant was Feb. 1, 2022, when the claimed plant was displayed as a photograph with a non-enabling brief description on a website maintained by Walters Gardens, Inc., who obtained the plant and all information relating thereto, from the inventor. The first plants sold of *Bergenia* 'Fairytale Romance' were by Walters Gardens, Inc. on Aug. 22, 2022. Walters Gardens, Inc. obtained the new plant and all information about the new plant directly from the inventor. No other plants have been sold earlier than this date anywhere in the world, nor has any disclosure of the new plant been made more than one year prior the filing date of this application, and such disclosure within one year was either derived directly or indirectly from the inventor.

BACKGROUND OF THE PLANT

The present invention relates to the new and distinct Heartleaf *Bergenia* herein also referred to as *Bergenia* 'Fairytale Romance', by the cultivar name, 'Fairytale Romance', or as the new plant. The new plant was hybridized by the inventor on Apr. 20, 2014, from a cross-pollination plant of *Bergenia* 'Angle Kiss' (not patented) as the female or seed parent and 'Winterglut' (not patented) as the male or pollen parent. The cross was performed in a greenhouse of a wholesale perennial grower in Zeeland, Mich. The single seedling represented by 'Fairytale Pink' was selected from a group of seedlings by the inventor, isolated, compared in subsequent years to other *Bergenia* and subsequently found to be different from all cultivars known to the discoverer, and given the breeder code 14-11-1 through the remaining evaluation process.

Asexual propagation at the same nursery in Zeeland, Mich., USA initially by basal cuttings and later by shoot tip sterile tissue culture has shown 'Fairytale Romance' to be stable and reproduce true to type in successive generations since late summer of 2016.

SUMMARY OF THE PLANT

*Bergenia* 'Fairytale Romance' has not been observed in all possible environmental conditions. The phenotype may vary slightly with changes in environments such as light intensity, fertility, water availability, etc. without, however any variation in genotype.

*Bergenia* 'Fairytale Romance' is distinct from all cultivars known to the inventor in the following traits:

1. Dense mounded habit;
2. Medium-sized, densely-arranged, deep-green, glossy, obovate, evergreen foliage;
3. Heavily-branched, large panicles of large, apple-blossom-pink, campanulate flowers over a long period in spring;
4. Medium growth rate;
5. Naturally resistant to deer and rabbit.

Plants of *Bergenia* 'Fairytale Romance' are most similar to: 'Apple Blossom' U.S. Plant Pat. No. 15,101, 'Bressingham Ruby' U.S. Plant Pat. No. 7,344, 'Flirt' U.S. Plant Pat. No. 26,355, 'Lunar Glow' U.S. Plant Pat. No. 20,247, 'Miss Piggy' U.S. Plant Pat. No. 32,132, 'Pink Dragonfly' (not patented), and 'Spring Fling' U.S. Plant Pat. No. 26,337.

'Flirt' has a smaller habit, smaller foliage, and smaller inflorescences with darker purplish-pink flowers. 'Bressingham Ruby' has a smaller and flatter habit with smaller inflorescences of deeper purplish-red. 'Pink Dragonfly' has narrower foliage and smaller habit with deeper pink flowers on smaller inflorescences. 'Miss Piggy' has a slightly smaller habit and deeper pink flowers.

The female parent, 'Angel Kiss', has a smaller habit with shorter, smaller peduncles, much smaller foliage. The male parent, 'Winterglut' has darker magenta-colored and smaller flowers on taller peduncles, and the winter foliage has more burgundy coloration.

BRIEF DESCRIPTION OF THE DRAWINGS

The color drawings illustrate the overall characteristics of *Bergenia* 'Fairytale Romance' as a three-year-old plant. The colors are as true as reasonably possible given the technology available. The color values may vary slightly depending on light intensity and quality.

DETAILED BOTANICAL DESCRIPTION

Figure 1:
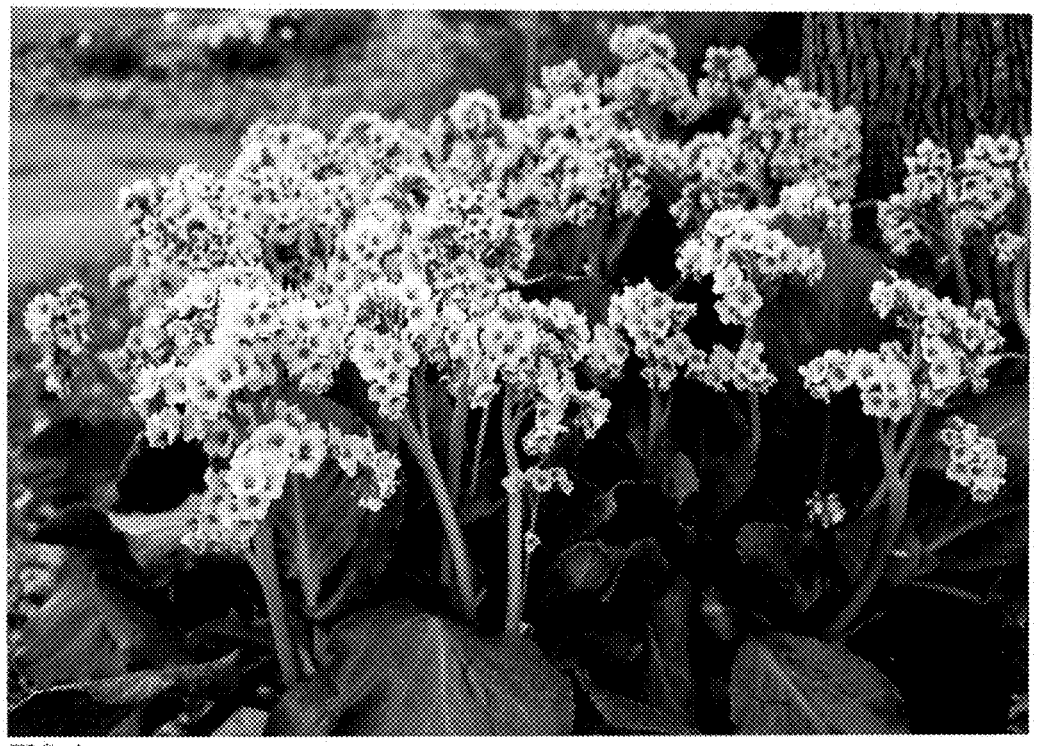
FIG. 1 shows the new plant in a landscape environment.
Figure 2:
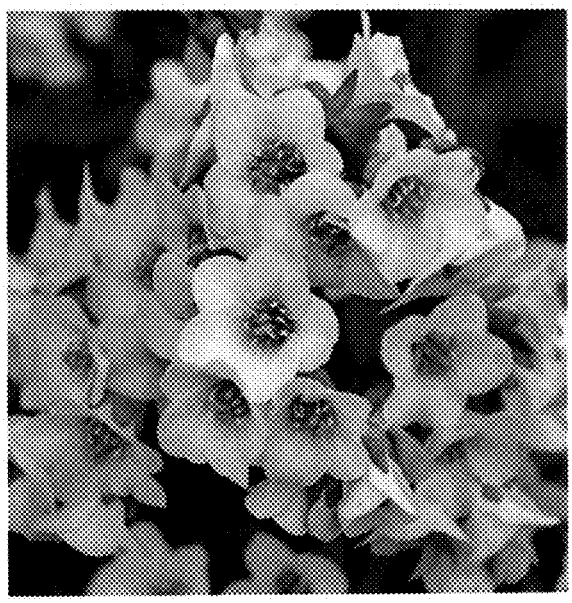
FIG. 2 shows a close-up of the flowers of the new plant.

The following description is based on two-year-old plants growing in a partially-shaded greenhouse and in an outdoor shaded trial garden in Zeeland, Mich., USA. Except for ordinary dictionary color usage, color references are according to The Royal Horticultural Society Colour Chart, 2015 edition. The new plant has not been observed in all possible growing conditions and may vary in phenotypic characteristics based on water availability, light conditions, fertilizer, temperatures, etc. without varying in genotypic characteristics.

Parentage: Female or seed parent 'Angel Kiss'; male or pollen parent 'Winterglut';

Asexual propagation: Division of tissue culture plants, about 21 days to initiate roots; time to finish 25 mm plugs in a one-gallon container about 3 months; moderate growth rate;

Plant habit: Low, spreading, herbaceous, evergreen, winter-hardy, perennial mound; with heavily branched flower stems; with about 6 shoots per plant; shoots to about 5 cm long and about 3 cm diameter;

Plant size: Foliage up to about 56 cm wide and about 38 cm tall; flowering to about 50 cm wide and about 40 cm tall;

Leaves: Alternate; simple; coriaceous; obovate to ovate; adaxial and abaxial surface lustrous; rounded apex; cuneate base; margin irregularly dentate to crenate; to 26 cm long and 20 cm wide, average about 20.5 cm long and about 15 cm wide;

Leaf color: Young expanding leaves adaxial nearest blend of RHS 138A and RHS 144A and abaxial between RHS 144A and RHS 146B; mature leaves adaxial nearest RHS 139A, abaxial between RHS 143A and RHS 138A; winter color developing variable, moderate to strong blush of nearest RHS 187A adaxial and nearest RHS 187B abaxial;

Veins: Pinnate;

Vein color: Adaxial basally blend between RHS 144A and RHS 143C, distally becoming RHS 139A, abaxial basally nearest blend between RHS 146D and RHS N144D, distally becoming nearest RHS 146C;

Inflorescence: Panicle; about 6 per plant; to about 40 cm long and 8 mm diameter at base, flowering portion to about 10 cm tall and 9 cm wide; cylindrical; lustrous; sparsely minutely hispidulous to glabrous;

Peduncle color: Variable, proximal portion nearest blend of RHS 145C and RHS 146D, distally nearest RHS 146D with minor to blushing to nearly solid nearest RHS 178B;

Flower: Single; perfect; campanulate; on terminal branches; about 24 mm across, about 16 mm long; attitude outright to slightly drooping;

Flower fragrance: None detected;

Calyx: Campanulate; to about 13 mm wide and 10 mm long;

Sepals: Typically, five, rarely six or seven; ovate; broadly acute apex; truncate base; margin entire; glabrous and lustrous adaxial and abaxial; about 12 mm long and about 4.5 mm wide;

Sepal color: Adaxial nearest RHS 146C with thin marginal rim nearest RHS 184B, abaxial nearest RHS 178B; abaxial nearest RHS 146C in the longitudinal center, with margins of nearest RHS 184B to nearly solid RHS 180A, and base nearest RHS 180A;

Flowering period: Beginning early spring, for about 4 weeks; producing up to 25 flowers per branch and up to 90 flowers per panicle;

Individual flower longevity: 7 to 10 days;

Flower buds one day prior to opening: Oblong, acute apex, about 18 mm long and 7 mm diameter;

Flower bud color one day prior to opening: Exposed petals nearest RHS 68B, sepals nearest RHS 180A with an undertone or nearest. RHS 146C;

Pedicel: Cylindrical; glaucous; lustrous; average about 4 mm long and 2 mm diameter;

Pedicel color: Variable; nearest RHS 146C with blush of nearest RHS 180A to nearly solid RHS 180A;

Petals: Typically, five in a single whorl, rarely six; obovate; rounded apex; attenuate to cuneate base; margin entire; glabrous adaxial abaxial; imbricate near longitudinal middle; about 14 mm long and 10 mm wide near middle;

Petal color: Variable; when initially open adaxial between RHS 68C and RHS 68B transitioning to nearest a blend of RHS NN155D to RHS 68B with some small patches of nearest RHS 68B, abaxial between RHS 69B and RHS 68B with midrib of nearest RHS 68B; mature adaxial and abaxial between RHS 68B and RHS NN155D with basal region around midribs nearest RHS NN155D;

Androecium: Typically, ten; about 12.0 mm long;

*Filament*.—About 7 mm long and 0.7 mm diameter; color initially translucent and nearest RHS 157C maturing to nearest RHS 68A distally and RHS 157D proximally.

*Anther*.—Ellipsoidal; basifixed; longitudinal; about 2.5 mm long and 1 mm across; color nearest RHS 158B.

*Pollen*.—Abundant; color nearest RHS 20C.

Gynoecium: Double; about 14 mm long;

*Ovary*.—Partly inferior.

*Style*.—Cylindrical; about 8 mm long and 4.5 mm diameter above ovary; color nearest RHS 146D.

*Stigma*.—Loosely lobed; about 3.0 mm wide, 1.0 mm across, and 1.0 mm tall; color nearest initially between RHS 146D and RHS N144D, at flower maturity nearest RHS 176B.

Seed: Ellipsoidal; acute apex and rounded base; surface glabrous; about 2.0 mm long and 0.5 mm across center; color nearest RHS 200B;

*Bergenia* 'Fairytale Romance' is tolerant of winter temperatures from USDA hardiness at least from zones 4 to 8. The new plant grows best with good drainage and adequate moisture. It is not known to be tolerant of diseases and pests that are common to other Heartleaf *Bergenia* cultivars.

I claim:

1. A new and distinct cultivar of *Bergenia* plant named 'Fairytale Romance' as described and illustrated.

* * * * *